United States Patent
Wickham et al.

(10) Patent No.: US 11,013,536 B2
(45) Date of Patent: May 25, 2021

(54) FASTENER ASSEMBLY INCLUDING CONTACT PIN

(71) Applicant: WARSAW ORTHOPEDIC, INC., Warsaw, IN (US)

(72) Inventors: Jeffrey Wickham, Ooltewah, TN (US); Mark Dace, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 88 days.

(21) Appl. No.: 16/395,319

(22) Filed: Apr. 26, 2019

(65) Prior Publication Data

US 2020/0337736 A1    Oct. 29, 2020

(51) Int. Cl.
*A61B 17/70*    (2006.01)

(52) U.S. Cl.
CPC ...... *A61B 17/7034* (2013.01); *A61B 17/7035* (2013.01)

(58) Field of Classification Search
CPC ............ A61B 17/7032; A61B 17/7034; A61B 17/7035; A61B 17/7037; A61B 17/704
See application file for complete search history.

(56) References Cited

U.S. PATENT DOCUMENTS

| | | | |
|---|---|---|---|
| 9,707,013 B2 | 7/2017 | Rezach et al. | |
| 9,872,711 B2 | 1/2018 | Hynes et al. | |
| 9,883,948 B2 | 2/2018 | Chavarria et al. | |
| 9,949,776 B2 | 4/2018 | Mobasser et al. | |
| 9,962,171 B2 | 5/2018 | Rezach et al. | |
| 9,974,569 B2 | 5/2018 | Lehmann, Jr. et al. | |
| 9,993,270 B2 | 6/2018 | Butler | |
| 10,028,770 B2 | 7/2018 | Rezach et al. | |
| 10,172,650 B2 | 1/2019 | Hynes et al. | |
| 2006/0241596 A1 | 10/2006 | Rezach | |
| 2007/0233138 A1 | 10/2007 | Figueroa et al. | |
| 2011/0178559 A1* | 7/2011 | Barry ................ | A61B 17/7032 606/302 |
| 2012/0065691 A1 | 3/2012 | Simonson | |
| 2017/0245898 A1 | 8/2017 | May et al. | |

FOREIGN PATENT DOCUMENTS

JP    2004-512899    4/2004

OTHER PUBLICATIONS

International Search Report and Written Opinion dated Feb. 11, 2020 from corresponding International Application No. PCT/US2019/057576.
U.S. Appl. No. 15/843,938, filed Dec. 15, 2017 in the name of May et al.
U.S. Appl. No. 16/287,700, filed Feb. 27, 2019 in the name of Rezach et al.
U.S. Appl. No. 16/380,739, filed Apr. 10, 2019 in the name of Rezach et al.
U.S. Appl. No. 16/386,328, filed Apr. 17, 2019 in the name of Rezach et al.
U.S. Appl. No. 16/395,409, filed Apr. 26, 2019 in the name of Wickham et al.

* cited by examiner

*Primary Examiner* — Eduardo C Robert
*Assistant Examiner* — Christina NegrelliRodriguez

(57) ABSTRACT

A bone fastener assembly including a bone screw, a receiver, a crown, a seat, and a contact pin is provided. The contact pin is formed as a leaf spring resiliently biased in a first position that affords generation of spring force via deformation thereof, and the contact pin acts as a tensioner to ultimately press against a head portion of the screw to aid movement prevention of the head portion relative to the receiver.

20 Claims, 4 Drawing Sheets

FASTENER ASSEMBLY INCLUDING CONTACT PIN

FIELD

The present technology is generally related to a fastener assembly including a contact pin.

BACKGROUND

Multi-axial screw assemblies are used to facilitate placement and attachment of spinal rods relative to the spine. The spinal rods can be used in correcting spinal abnormalities. Typically, such multi-axial screw assemblies include at least a bone screw portion and a receiver portion attached to one another. The bone screw portions are attached to vertebrae, and the receiver portions receive portions of the spinal rods. Furthermore, the receiver portions of typical pedicle screw assemblies are angularly and fixedly positionable with respect to the screw portions to afford attachment of the spinal rods between vertebrae. The receiver portion is angularly/pivotally positionable relative to a screw portion prior to being fastened to a rod. However, without some friction between those components, the receiver portion would potentially flop freely relative to the screw portion. Therefore, there is a need for a contact pin portion receivable within the receiver portion that can provide enough friction between the components so that the receiver portion can be adjusted to approximately the final position and the components will stay in that position.

SUMMARY

The techniques of this disclosure generally relate to a contact pin used in fastener assemblies to aid in maintaining the angular/pivotal position of a screw and a receiver relative to one another.

In one aspect, the present disclosure provides a bone fastener assembly including a bone screw including a head portion, a threaded shaft portion, and a central axis, the head portion including an exterior surface; a receiver including a body portion, a first arm portion, and a second arm portion, the body portion having a first end, an opposite second end, and an interior surface defining a first cavity extending between the first end and the second end, the first arm portion including a first interior arm surface and the second arm portion including a second interior arm surface, the first interior arm surface and the second interior arm surface defining a second cavity therebetween, the first cavity and the second cavity communicating with one another; a crown including a first end, an opposite second, an exterior surface, and an interior surface defining at least a first interior cavity portion extending from the first end of the crown to a position intermediate the first end and the second end of the crown; a seat included in the receiver; and a contact pin having a first end, a second end, and a length between the first end and the second end, the contact pin being resiliently biased in a first configuration; where, when the bone fastener assembly is assembled, at least a portion of the crown is positioned within the first cavity of the receiver at a position at and adjacent the second end of the body portion, the contact pin is positioned within the first cavity of the receiver at a position between the crown and the seat; at least a portion of the head portion is receivable between the crown and the seat and positionable adjacent the contact pin, and the exterior surface of the head portion contacts at least the seat and the contact pin; and where the contact pin contacts the head portion of the screw and presses the exterior surface of the head portion of the screw against the interior surface of the first cavity of the receiver.

In another aspect, the disclosure provides a bone fastener assembly including a bone screw including a head portion, a threaded shaft portion, and a central axis, the head portion including an exterior surface; a receiver including a body portion having a first end, an opposite second end, and an interior surface defining a first cavity extending between the first end and the second end; a crown including a first end, an opposite second, an exterior surface, and an interior surface defining at least a first interior cavity portion extending inwardly from the first end of the crown; a seat included in the receiver; and a contact pin having a first end, a second end, and a length between the first end and the second end, the contact pin being resiliently biased in a first configuration; where, when the bone fastener assembly is assembled, at least a portion of the crown is positioned within the first cavity of the receiver at a position at and adjacent the second end of the body portion, at least a portion of the head portion is receivable between the crown and the seat, and at least a portion of the contact pin contacts the exterior surface the head portion.

In yet another aspect, the disclosure provides a bone fastener assembly including a bone screw including a head portion, a threaded shaft portion, and a central axis, the head portion including an exterior surface; a receiver including a body portion having a first end, an opposite second end, and an interior surface defining a first cavity extending between the first end and the second end; a seat included in the receiver; and a contact pin having a first end, a second end, and a length between the first end and the second end, the contact pin being resiliently biased in a first configuration; where, when the bone fastener assembly is assembled, at least a portion of the head portion is receivable between the seat and the second end of the body portion, and at least a portion of the contact pin extends into the first cavity of the receiver and contacts the exterior surface of the head portion to press the exterior surface of the head portion of the screw against the interior surface of the first cavity of the receiver.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
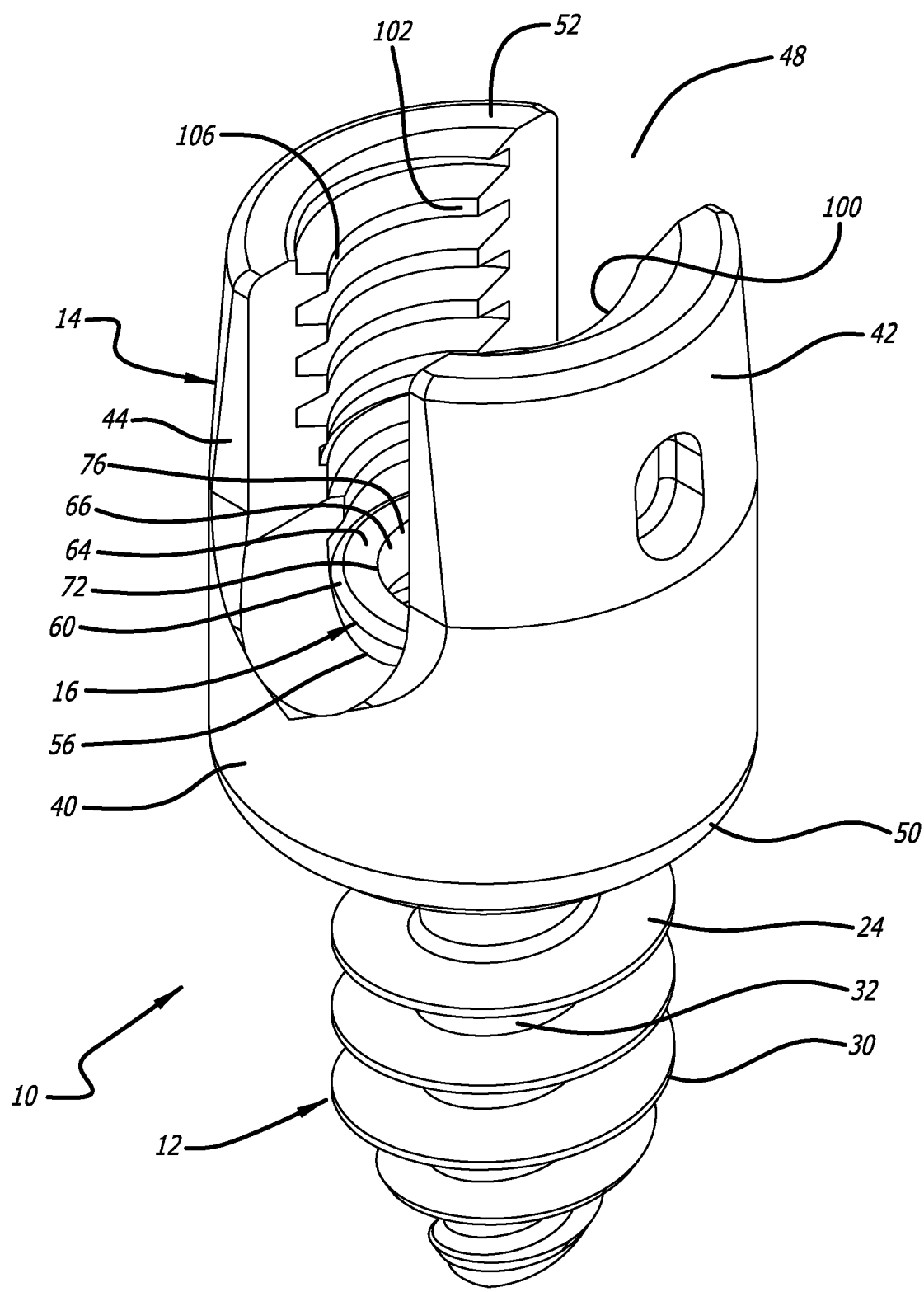
FIG. 1 is a top, front perspective view that illustrates an embodiment of a fastener assembly.
Figure 2:
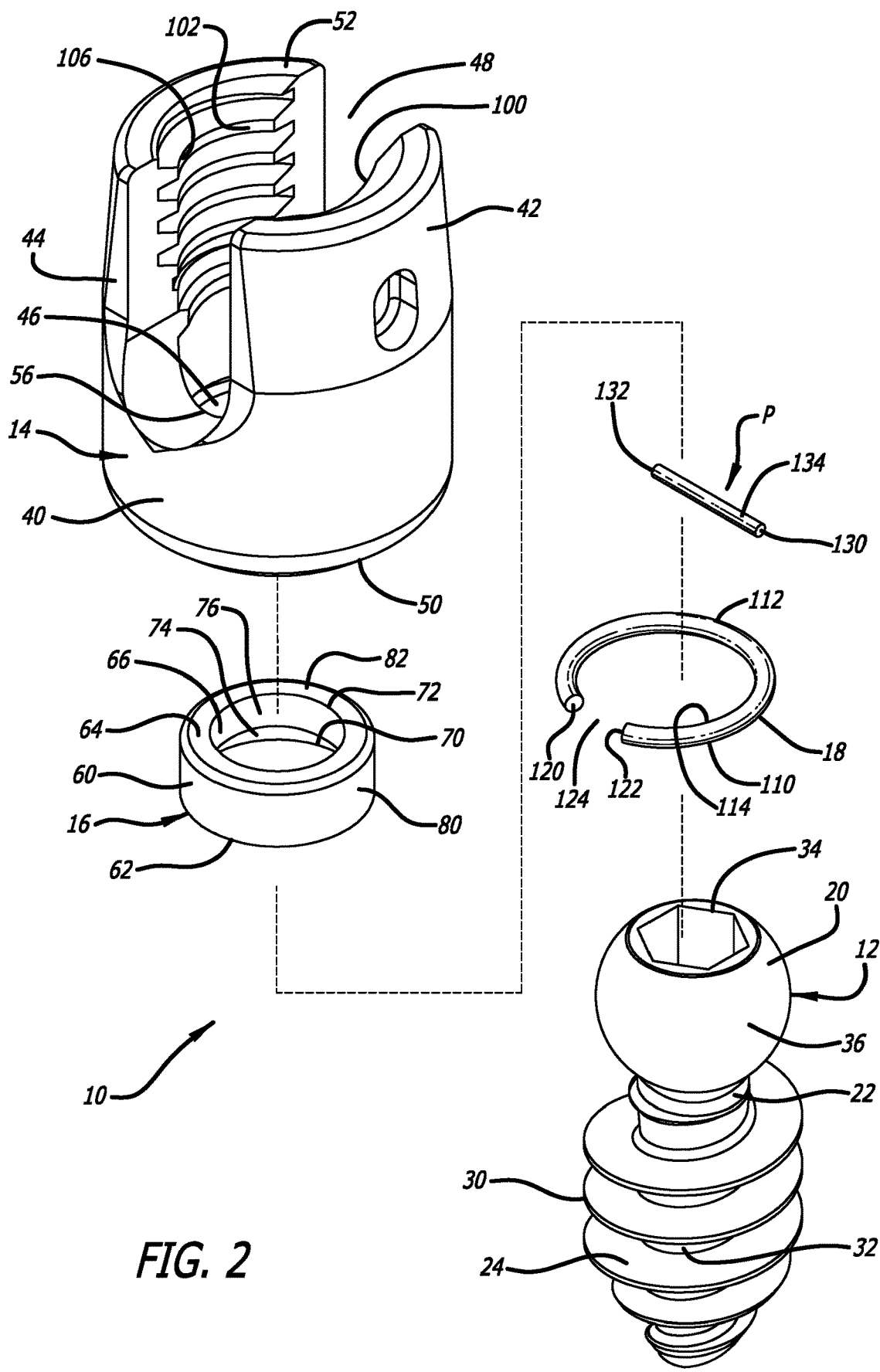
FIG. 2 is a top, front, exploded perspective view that illustrates the fastener assembly of FIG. 1.
Figure 3:
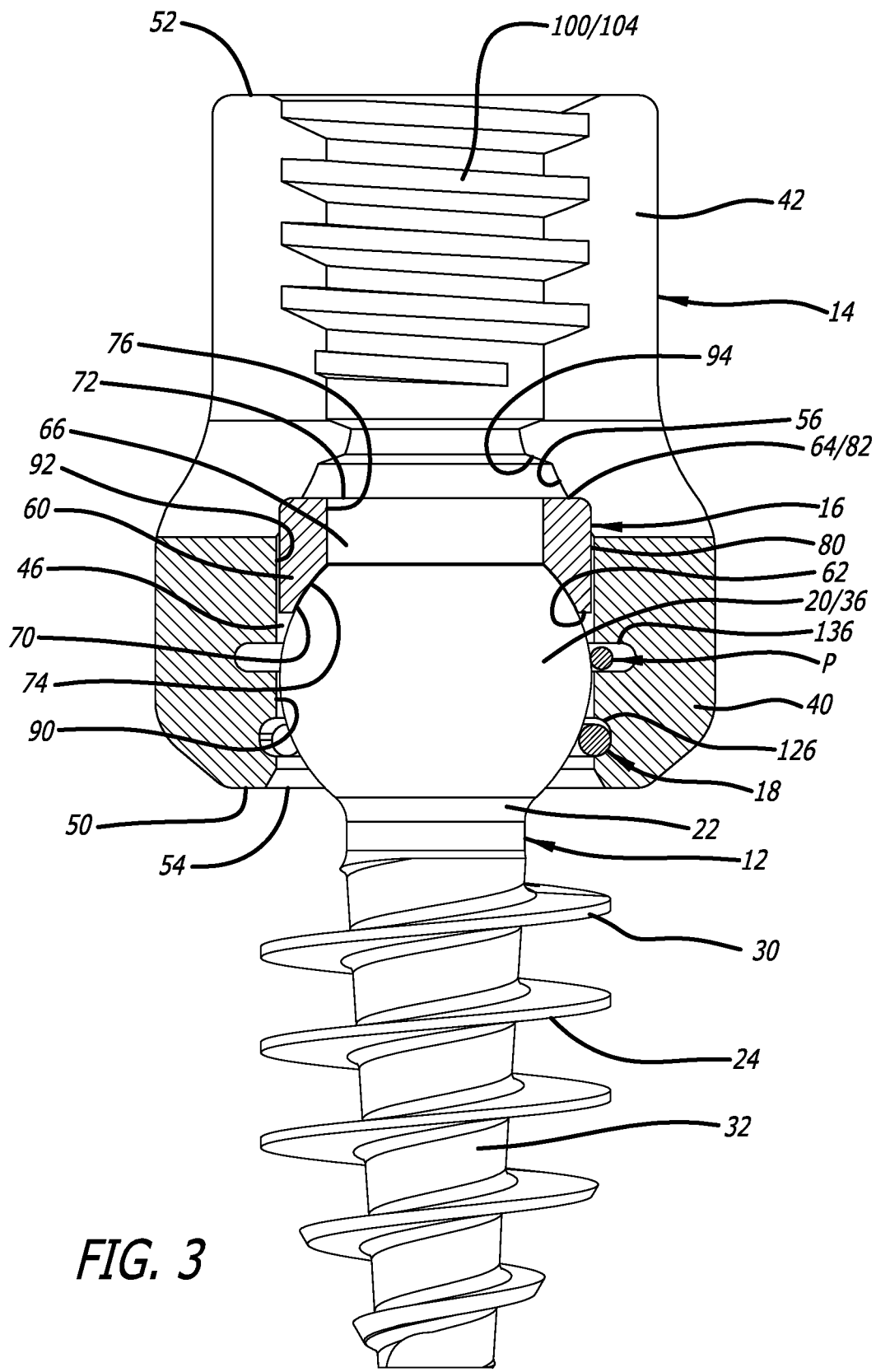
FIG. 3 is a front, elevational, first cross-sectional view that illustrates the fastener assembly of FIG. 1.

A fastener assembly according to an embodiment of the present disclosure is generally indicated by the numeral 10 in FIGS. 1-3. The fastener assembly 10 can be a multi-axial screw assembly, and includes a bone screw 12, a receiver 14, a crown 16, an expansion (or retaining) ring 18, and a contact pin P. As depicted in FIG. 3, when the fastener assembly 10 is assembled, the crown 16, the expansion ring 18, and the contact pin P are positioned within the receiver 14, and a portion of the screw 12 is receivable within receiver 14 between the crown 16 and the expansion ring 18 and adjacent the contact pin P to attach the screw 12 and the receiver 14 to one another. The fastener assembly 10 is configured to afford angular/pivotal adjustment of the screw 12 and the receiver 14 relative to one another into a selected angular/pivotal position.

The fastener assembly 10 is used in facilitating attachment of a spinal construct such as a spinal rod (not shown) to the spine. A portion of the spinal rod is ultimately received within the receiver 14, and a threaded cover (not shown) engaging the receiver 14 is positioned over the portion of the spinal rod to retain the portion of the spinal rod within the receiver 14. Ultimately, the threaded cover pushes the portion of the surgical rod received in the receiver 14 against the crown 16 to force the crown 16 against the screw 12 and force the screw 12 against the expansion ring 18. As depicted in FIG. 3, such contact of the crown 16 against the screw 12 and the screw 12 against the expansion ring 18, along with the engagement of the screw 12 with the contact pin P as well as the receiver 14, ultimately serves in fixedly attaching the screw 12 and the receiver 14 to one another in a selected angular/pivotal position with respect to one another. Moreover, before the fixed attachment of the screw 12 and the receiver 14, the contact pin P can be used to hold the screw 12 and the receiver 14 in position relative to one another during adjustment as the angular/pivotal position of the screw 14 and the receiver 14 is being selected.

The screw 12 can be used to facilitate fixed attachment of the receiver 14 and the crown 16 to tissue such as, for example, bone. For example, the screw 12 can be a pedicle screw, or as depicted in FIGS. 1-3, a lateral mass screw. Furthermore, the screw 12 includes a head portion 20, a neck portion 22, a shaft portion 24, and a central axis. As depicted in FIGS. 2 and 3, the head portion 20 can be generally spherical, the neck portion 22 joins the shaft portion 24 to the head portion 20, and the shaft portion 24 is configured to penetrate tissue such as, for example, bone. The shaft portion 24 can include one or more thread forms 30 having a continuous turn or discrete turns and/or different pitches around a shank 32 to facilitate such bone penetration. Besides facilitating bone penetration, the thread form 30 is used in securing the screw 12 and the receiver 14 to the bone. Furthermore, the shank 32 can have a smaller or a larger diameter than the neck portion 22, and can include portion(s) having tapered and/or cylindrical configurations.

The head portion 20 includes a tool-engaging portion 34 configured to engage a surgical tool or instrument for rotating the screw 12 to facilitate penetration of the screw 12 into tissue such as, for example, bone. The tool-engaging portion 34 includes six (6) lobes arranged in a generally hexagonal cross-sectional configuration. In some embodiments, the tool-engaging portion 34 can have, for example, alternative cross-sectional configurations such as being generally polygonal (including generally triangular, rectangular, hexagonal, etc. configurations), oval, or irregular.

Furthermore, the head portion 20 includes an exterior surface 36, and, as depicted in FIGS. 2 and 3, the exterior surface 36 can be generally spherical. The receiver 14 can be angularly/pivotally adjustable on the exterior surface 36 of the head portion 20. Thus, after penetration of the screw 12 into tissue such as, for example, bone, the angular/pivotal position of the receiver 14 on the exterior surface 36 of the head portion 20 can be adjusted into the selected angular/pivotal position of the screw 14 and the receiver 14. Friction caused by the ultimate engagement, as depicted in FIG. 3, of the exterior surface 36 with the contact pin P, the receiver 14, the crown 16, and the expansion ring 18 serves in maintaining the position of the receiver 14 relative to the head portion 20 of the screw 12.

Figure 4:
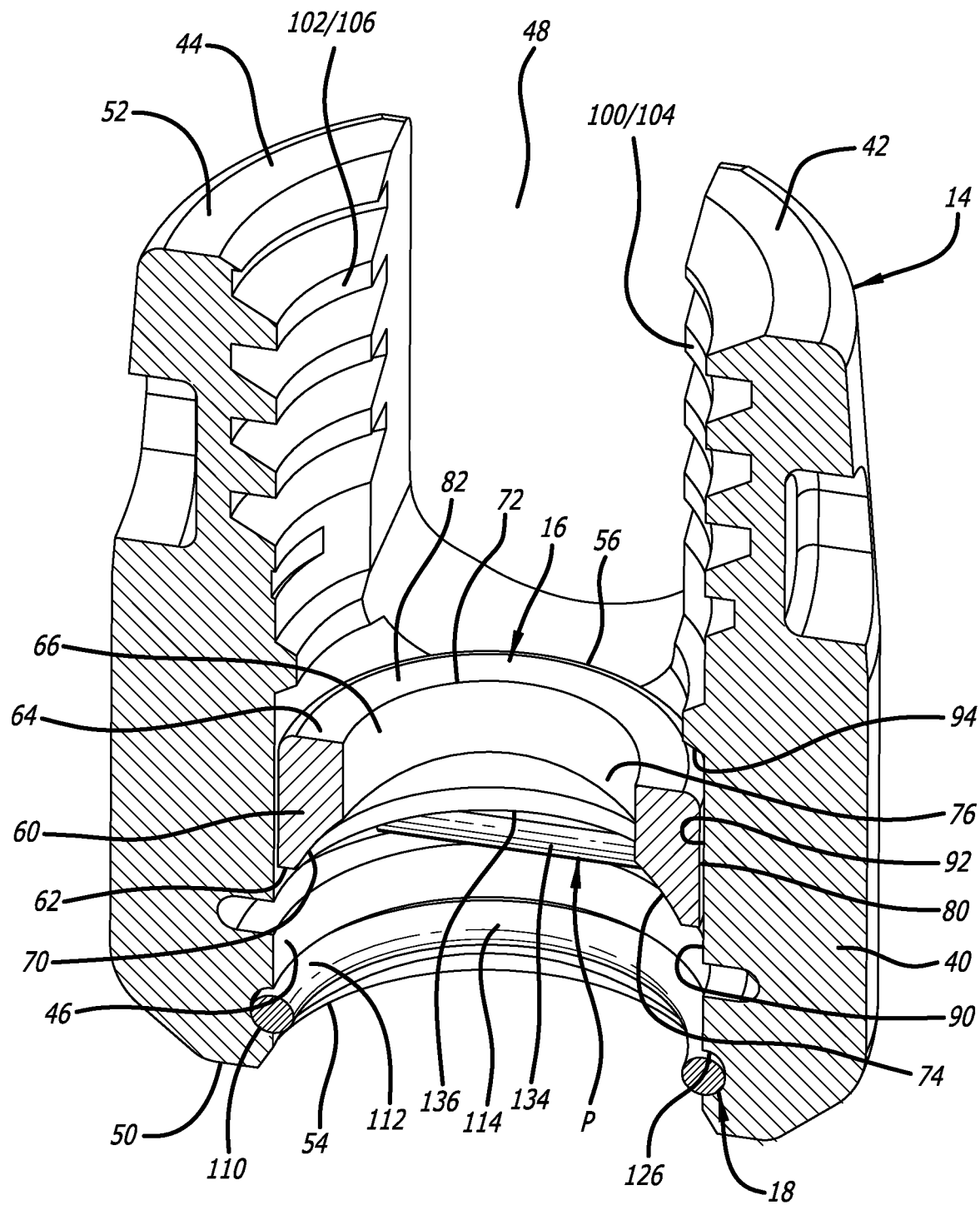
FIG. 4 is a front, perspective, second cross-sectional view that illustrates an assembly of a receiver, a crown, an expansion ring, and a contact pin of the fastener assembly of FIG. 1.

As depicted in FIGS. 1, 2, and 4, the receiver 14 includes a body portion 40, a first arm 42 extending upwardly from the body portion 40, and a second arm 44 extending upwardly from the body portion 40. The receiver 14 includes a first cavity 46 and a second cavity 48 that together extend between a first end 50 and a second end 52 of the receiver 14. The first cavity 46 is internal to the body portion 40, and extends between a first opening 54 and a second opening 56 in the body portion 40. The first opening 54 is at the first end 50 of the receiver 14, and the second opening 56 is intermediate the first end 50 and the second end 52 of the receiver 14. Furthermore, the second cavity 48 is formed between the first arm 42 and the second arm 44. As discussed below, the crown 16 is initially received in portions of the first cavity 46 and the second cavity 48 and then ultimately received in the first cavity 46, at least portions of the head portion 20 and the neck portion 22 are received in the first cavity 46, and a portion of the spinal rod is ultimately received in the second cavity 48.

As depicted in FIGS. 2-4, the crown 16 includes a wall portion 60 having a first end 62 and a second end 64 and an internal cavity 66 extending through the wall portion 60 between a first opening 70 formed at the first end 62 of the crown 16, and a second opening 72 formed at the second end 64 of the crown 16.

The wall portion 60 includes a first interior surface 74, a second interior surface 76, a first exterior surface 80, and a second exterior surface 82. The first interior surface 74 and the second interior surface 76 define the internal cavity 66, the first interior surface 74 can be spherical or generally spherical to facilitate engagement with the generally-spherical shape of the exterior surface 36 of the head portion 20, and the second interior surface 76 can be generally cylindrical to afford passage of a surgical tool or instrument. Friction caused by the ultimate engagement, as depicted in FIG. 3, of the exterior surface 36 with the interior surface 74 (along with the ultimate engagement of the exterior surface 36 with the contact pin P, the receiver 14, and the expansion ring 18) serves in maintaining the position of the head portion 20 relative to the receiver 14. Furthermore, as depicted in FIG. 2, the first exterior surface 80 can be generally cylindrical, and the second exterior surface 82 can be generally flat. The generally cylindrical shape of the first exterior surface 80 can facilitate engagement with similarly contoured portions of the receiver 14 in the first cavity 46, and a portion of the spinal rod received in the second cavity 48 is ultimately contacted to the exterior surface 82.

As depicted in FIGS. 3 and 4, the first cavity 46 formed in the body portion 40 of the receiver 14 is defined by an interior surface 90, the first opening 54, and the second opening 56. The interior surface 90 can be sized to receive the crown 16. The interior surface 90 includes a generally cylindrical portion 92 and at least one shoulder portion 94. Upon insertion of the crown 16 into the first cavity 46, the first exterior surface 80 of the crown 16 interfaces with the portion 92 of the interior surface 90, and the at least one shoulder portion 94 prevents the crown 16 from exiting the first cavity 46. Furthermore, upon insertion of a portion of the head portion 20 into the first cavity 46, the exterior surface 36 contacts the portion 92 of the interior surface 90. Friction caused by the ultimate engagement, as depicted in FIG. 3, of the exterior surface 36 of the head portion 20 with the portion 92 of the interior surface 90 (along with the ultimate engagement of the exterior surface 36 with the contact pin P, the crown 16, and the expansion ring 18) serves in maintaining the position of the head portion 20 relative to the receiver 14.

As depicted in FIG. 4, the second cavity 48 is formed between the first arm 42 and the second arm 44 by a first interior surface 100 formed on the first arm 42 and a second interior surface 102 formed on the second arm 44. The second cavity 48 includes first threads 104 and second threads 106 formed on the first interior surface 100 of the first arm 42 and the second interior surface 102 of the second arm 44, respectively, for engaging the threaded cover. When a portion of the spinal rod is received in the second cavity 48, the threaded cover can be engaged to the first threads 104 and the second threads 106 to facilitate attachment of the portion of the spinal rod received in the second cavity 48 to the fastener assembly 10.

The expansion ring 18 serves as a seat for seating a portion of the head portion 20, and the expansion ring 18 is formed as an incomplete generally annular structure that affords expansion and contraction thereof. As depicted in FIG. 2, the expansion ring 18 includes a first end 110, an opposite second end 112, and an aperture 114 extending between the first end 110 and the second end 112. Furthermore, the expansion ring 18 is incomplete, and includes a first circumferential end portion 120, a second circumferential end portion 122, and a gap 124 between the first circumferential end portion 120 and the second circumferential end portion 122. The expansion ring 18 defines the aperture 114, and the aperture 114 is configured to receive a portion of the screw 12.

The expansion ring 18 is ultimately received at least partially in the space defined by a recess 126 formed in the portion 92 of the interior surface 90 adjacent the first opening 54 in the body portion 40. To that end, the expansion ring 18 is compressible between at least an expanded first position and a compressed second position to decrease the size of the gap 124, and hence, decrease the size of the aperture 114. The expansion ring 18 can be initially threaded onto the screw 12 to be received around the neck portion 22. When received around the neck portion 22, and upon insertion of a portion of the head portion 20 into the first cavity 46, the expansion ring 18 can be compressed to fit through the first opening 54. Thereafter, the expansion ring 18 can be moved along the portion 92 of the interior surface 90 until it reaches the recess 126, where the expansion ring 18 expands into the space defined by the recess 126. Friction caused by the ultimate engagement, as depicted in FIG. 3, of the exterior surface 36 of the head portion 20 with the expansion ring 18 (along with the ultimate engagement of the exterior surface 36 with the contact pin P, the receiver 14, and the crown 16) serves in maintaining the position of the head portion 20 relative to the receiver 14.

The contact pin P can be formed as a leaf spring resiliently biased in a first position that affords generation of spring force via deformation thereof, and, as depicted in FIG. 3, the contact pin P acts as a tensioner to ultimately press against the head portion 20 of the screw 12 to aid movement prevention of the head portion 20 relative to the receiver 14.

As depicted in FIG. 2, the contact pin P includes a first end 130, a second end 132, and a length 134 between the first end 130 and the second end 132. The contact pin P can be substantially straight or curved along its length, and the contact pin P is at least partially received in at least one groove 136 formed in the portion 92 of the interior surface 90 intermediate the first opening 54 and the second opening 56 in the body portion 40. The groove 136 is configured in shape and size to at least partially receive the contact pin P.

When portions of the contact pin P, as depicted in FIG. 4, are received in the groove 136, a portion of the length 134 extends into the first cavity 46. More specifically, at least a portion of the contact pin P adjacent the first end 130 can be received in the groove 136, at least portion of the contact pin P adjacent the second end 132 can be received in the groove 136, and at least a portion of the length 134 extending between the portions received in the groove 136 is positioned in the first cavity 46.

The contact pin P, as discussed above, is a leaf spring, and, given that a portion thereof extends into the cavity, the contact pin P ultimately forms an interference fit with a portion of the head portion 20 received in the first cavity 46. When a portion of the head portion 20 is received in the first cavity 46, as depicted in FIG. 3, the contact pin P contacts the exterior surface 36 of the head portion 20, and the spring force thereof presses portions of the exterior surface 36 (generally opposite from the contact of the contact pin P) against the portion 92 of the interior surface 90 of the first cavity 46. The contact pin P can deform via deflection to generate the spring force for pressing against the exterior surface 36 of the head portion 20. Friction created by the ultimate engagement, as depicted in FIG. 3, of the contact pin P with the exterior surface 36 and of the exterior surface 36 with the portion 92 of the interior surface 90 generally opposite from the contact of the contact pin P (along with the ultimate engagement of the exterior surface 36 with the crown 16 and the expansion ring 18) serves in maintaining the position of the head portion 20 in the first cavity 46. Furthermore, the friction created by use of the contact pin P can be used to somewhat loosely hold the screw 12 and the receiver 14 in position relative to one another during adjustment as the angular/pivotal position of the screw 12 and the receiver 14 is being selected.

The fastener assembly 10 can be assembled with the crown 16, then the contact pin P, and then the head portion 20 of the screw 12, then the expansion ring 18 inserted through the first opening 54 and into the first cavity 46 of the receiver 14. To illustrate, the crown 16 is initially inserted through the first opening 54, into the first cavity 46, and positioned in a first position within the cavity. In the first position, the crown 16 is somewhat loose in the first cavity 46. The contact pin P is then inserted through the first opening 54, into the first cavity 46, and into the groove 136. Thereafter, a portion of the head portion 20 is inserted through the first opening 54 and into the first cavity 46, and the expansion ring 18 is inserted through the first opening 54, into the first cavity 46, and positioned in the recess 126. Upon initial installation, the head portion 20 is somewhat loosely held within the first cavity 46 between the interior surface 74 of the crown 16 and the expansion ring 18 by the contact of the contact pin P with the exterior surface 36 of the head portion 20 and the corresponding contact of the exterior surface 36 of the head portion 20 with the portion 92 of the interior surface 90 of the first cavity 46. The spring force of the contact pin P can hold the screw 12 and the receiver 14 in position relative to one another during adjustment as the angular/pivotal position of the screw 12 and the receiver 14 is being selected.

After the angular/pivotal position of the screw 12 and the receiver 14 is selected, a portion of the surgical rod is positioned in the second cavity 48, and threads of the threaded cover are threadably engaged to the first threads 104 and the second threads 106. Continued threadable engagement of the threaded cover with the first threads 104 and the second threads 106 pushes the portion of the surgical rod received in the receiver 14 against the crown 16. When the threaded cover pushes the portion of the surgical rod against the crown 16, the crown 16 is moved downwardly within the receiver 14. Such movement of the crown 16 pushes the interior surface 74 against the exterior surface 36 and the exterior surface 36 against the expansion ring 18 to trap at least a portion of the head portion 20 firmly in position between the crown 16 and the expansion ring 18. In doing so, a portion of the head portion 20 adjacent the neck portion 22 is seated against the expansion ring 18. Friction between the screw 12 and the expansion ring 18, and friction between the screw 12 and the crown 16 ultimately fixedly attaches the screw 12 and the receiver 14 and serves in maintaining the selected angular/pivotal position of the head portion 20 of the screw 12 in the cavity 46 relative to the receiver 14.

Furthermore, when at least a portion of the head portion 20 is positioned relative to the receiver 14, the crown 16, and the expansion ring 18, the contact pin P, as discussed above, contacts the exterior surface 36 of the head portion 20, and the spring force thereof presses portions of the exterior surface 36 (generally opposite from the contact of the contact pin P) against the portion 92 of the interior surface 90 of the cavity 46. The friction created by the contact of the contact pin P with the exterior surface 36 of the head portion 20 and the corresponding contact of the exterior surface 36 of the head portion 20 with the portion 92 of the interior surface 90 further serves in maintaining the selected angular/pivotal position of the head portion 20 of the screw 12 in the cavity 46 relative to the receiver 14.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A bone fastener assembly comprising:
   a bone screw including a head portion, a threaded shaft portion, and a central axis, the head portion including an exterior surface;
   a receiver including a body portion, a first arm portion, and a second arm portion, the body portion having a first end, an opposite second end, and an interior surface defining a first cavity extending between the first end and the second end, the first arm portion extending from at least adjacent the second end of the body portion and including a first interior arm surface, and the second arm portion extending from at least adjacent the second end of the body portion and including a second interior arm surface, the first interior arm surface and the second interior arm surface defining a second cavity therebetween, the first cavity and the second cavity communicating with one another;
   a crown including a first end, an opposite second end, an exterior surface, and an interior surface defining at least a first interior cavity portion extending from the first end of the crown to a position intermediate the first end and the second end of the crown;
   a seat included in the receiver and positioned adjacent the first end of the body portion; and
   a contact pin having a first end, a second end, and a length between the first end and the second end, the contact pin being positioned between the seat and the second end of the body portion, and the contact pin being resiliently biased in a first configuration;
   wherein, when the bone fastener assembly is assembled,
   at least a portion of the crown is positioned within the first cavity of the receiver at a position at and adjacent the second end of the body portion,
   the contact pin is positioned within the first cavity of the receiver at a position between the crown and the seat;
   at least a portion of the head portion is receivable between the crown and the seat and positionable adjacent the contact pin, and
   the exterior surface of the head portion contacts at least the seat and the contact pin; and
   wherein the head portion includes a maximum dimension perpendicular to the central axis, a first plane perpendicular to the central axis extends along the maximum dimension of the head portion, the first plane divides the head portion into a first portion and a second portion, and the first portion is closer to the shaft portion than the second portion, and wherein at least a portion of the contact pin contacts the second portion of the head portion and presses the exterior surface of the head portion of the screw against the interior surface of the first cavity of the receiver.

2. The bone fastener assembly of claim 1, wherein the interior surface of the first cavity of the receiver includes at least one groove positioned adjacent the second end of the body portion and sized to receive at least portions of the contact pin.

3. The bone fastener assembly of claim 2, wherein the first end, the second end, and portions of the length of the contact pin adjacent the first end and the second end are received in the at least one groove.

4. The bone fastener assembly of claim 3, wherein, when the first end and the second end of the contact pin are received in the at least one groove, a portion of the length of the contact pin extends into the first cavity of the receiver.

5. The bone fastener assembly of claim 4, wherein the portion of the length of the contact pin extending into the first cavity of the receiver forms an interference fit with the head portion of the screw.

6. The bone fastener assembly of claim 1, wherein the exterior surface of the head portion is substantially spherical, and contact of the exterior surface of the head portion with the seat affords pivotal movement of the bone screw relative to the seat.

7. The bone fastener assembly of claim 6, wherein, when the bone fastener assembly is assembled, the exterior surface of the head portion contacts the interior surface of the crown, and contact of the exterior surface of the head portion with the crown affords pivotal movement of the bone screw relative to the crown.

8. A bone fastener assembly comprising:
   a bone screw including a head portion, a threaded shaft portion, and a central axis, the head portion including an exterior surface;
   a receiver including a body portion having a first end, an opposite second end, and an interior surface defining a first cavity extending between the first end and the second end;

a crown including a first end, an opposite second end, an exterior surface, and an interior surface defining at least a first interior cavity portion extending inwardly from the first end of the crown;

a seat included in the receiver and positioned adjacent the first end of the body portion; and a contact pin having a first end, a second end, and a length between the first end and the second end, the contact pin being positioned between the seat and the second end of the body portion, and the contact pin being resiliently biased in a first configuration;

wherein the head portion includes a maximum dimension perpendicular to the central axis, a first plane perpendicular to the central axis extends along the maximum dimension of the head portion, the first plane divides the head portion into a first portion and a second portion, and the first portion is closer to the shaft portion than the second portion, and wherein, when the bone fastener assembly is assembled, at least a portion of the crown is positioned within the first cavity of the receiver at a position at and adjacent the second end of the body portion, at least a portion of the head portion is receivable between the crown and the seat, and at least a portion of the contact pin contacts the exterior surface of the second portion of the head portion.

9. The bone fastener assembly of claim 8, wherein the contact pin contacts the head portion of the screw and presses the exterior surface of the head portion of the screw against the interior surface of the first cavity of the receiver.

10. The bone fastener assembly of claim 8, wherein the interior surface of the first cavity of the receiver includes at least one groove positioned adjacent the second end of the body portion and sized to receive at least portions of the contact pin.

11. The bone fastener assembly of claim 10, wherein the first end, the second end, and portions of the length of the contact pin adjacent the first end and the second end are received in the at least one groove.

12. The bone fastener assembly of claim 11, wherein, when the first end and the second end of the contact pin are received in the at least one groove, a portion of the length of the contact pin extends into the first cavity of the receiver.

13. The bone fastener assembly of claim 12, wherein the portion of the length of the contact pin extending into the first cavity of the receiver forms an interference fit with the head portion of the screw.

14. The bone fastener assembly of claim 8, wherein the exterior surface of the head portion is substantially spherical, and contact of the exterior surface of the head portion with the seat affords pivotal movement of the bone screw relative to the seat.

15. The bone fastener assembly of claim 14, wherein, when the bone fastener assembly is assembled, the exterior surface of the head portion contacts the interior surface of the crown, and contact of the exterior surface of the head portion with the crown affords pivotal movement of the bone screw relative to the crown.

16. A bone fastener assembly comprising:

a bone screw including a head portion, a threaded shaft portion, and a central axis, the head portion including an exterior surface;

a receiver including a body portion having a first end, an opposite second end, and an interior surface defining a first cavity extending between the first end and the second end;

a seat included in the receiver and positioned adjacent the first end of the body portion; and a contact pin having a first end, a second end, and a length between the first end and the second end, the contact pin being positioned between the seat and the second end of the body portion, and the contact pin being resiliently biased in a first configuration;

wherein the head portion incudes a maximum dimension perpendicular to the central axis, a first plane perpendicular to the central axis extends along the maximum dimension of the head portion, the first plane divides the head portion into a first portion and a second portion, and the first portion is closer to the shaft portion than the second portion, and wherein, when the bone fastener assembly is assembled, at least a portion of the head portion is receivable between the seat and the second end of the body portion, and at least a portion of the contact pin extends into the first cavity of the receiver and contacts the exterior surface of the second portion of the head portion to press the exterior surface of the head portion of the screw against the interior surface of the first cavity of the receiver.

17. The bone fastener assembly of claim 16, wherein the interior surface of the first cavity of the receiver includes at least one groove, positioned adjacent to the second end of the body portion and sized to receive at least portions of the contact pin.

18. The bone fastener assembly of claim 17, wherein the first end, the second end, and portions of the length of the contact pin adjacent the first end and the second end are received in the at least one groove.

19. The bone fastener assembly of claim 18, wherein, when the first end and the second end of the contact pin are received in the at least one groove, a portion of the length of the contact pin extends into the first cavity of the receiver.

20. The bone fastener assembly of claim 19, wherein the portion of the length of the contact pin extending into the first cavity of the receiver forms an interference fit with the head portion of the screw.

* * * * *